US010780235B2

(12) United States Patent
O'Mahony et al.

(10) Patent No.: US 10,780,235 B2
(45) Date of Patent: Sep. 22, 2020

(54) SYRINGE PUMP ENGAGEMENT DETECTION APPARATUS AND METHODS (71) Applicant: GAMBRO LUNDIA AB, Lund (SE)

(72) Inventors: John O'Mahony, Maple Grove, MN (US); Joshua Chambers, Minneapolis, MN (US)

(73) Assignee: Gambro Lundia AB, Lund (SE)

( * ) Notice: Subject to any disclaimer, the term of this patent is extended or adjusted under 35 U.S.C. 154(b) by 220 days.

(21) Appl. No.: 16/056,961

(22) Filed: Aug. 7, 2018

(65) Prior Publication Data

US 2018/0339117 A1 Nov. 29, 2018

Related U.S. Application Data (62) Division of application No. 14/655,245, filed as application No. PCT/US2013/077926 on Dec. 27, 2013, now Pat. No. 10,065,003.

(60) Provisional application No. 61/746,697, filed on Dec. 28, 2012.

(51) Int. Cl.
*A61M 5/50* (2006.01)
*A61M 5/20* (2006.01)
*A61M 5/315* (2006.01)
*A61M 5/145* (2006.01)
*A61M 5/168* (2006.01)

(52) U.S. Cl.
CPC ........ *A61M 5/5086* (2013.01); *A61M 5/1452* (2013.01); *A61M 5/1458* (2013.01); *A61M 5/16854* (2013.01); *A61M 5/2053* (2013.01); *A61M 5/31515* (2013.01); *A61M 2205/14* (2013.01); *A61M 2205/332* (2013.01); *A61M 2205/3337* (2013.01)

(58) Field of Classification Search
CPC ............ A61M 5/5086; A61M 5/31515; A61M 5/16854; A61M 5/1458; A61M 2205/332; A61M 2205/14
See application file for complete search history.

(56) References Cited

U.S. PATENT DOCUMENTS

| 4,838,857 A | 6/1989 | Strowe |
| 5,245,096 A | 10/1993 | Rondelet |
| 5,533,981 A | 7/1996 | Mandro |

(Continued)

FOREIGN PATENT DOCUMENTS

| DE | 102013004860 | 9/2014 |
| EP | 0916353 | 5/1999 |

(Continued)

OTHER PUBLICATIONS

PCT Search Report and Written Opinion for PCT/US2013/077926 dated Mar. 21, 2014 (12 pages).

(Continued)

*Primary Examiner* — Bradley J Osinski
(74) *Attorney, Agent, or Firm* — Mueting Raasch Group (57) ABSTRACT Syringe pump apparatus and methods for detecting proper or improper engagement of a syringe pump drive system with a syringe in the syringe pump are disclosed. The apparatus and methods can determine proper or improper engagement between a drive system and the plunger of a syringe in a syringe pump by detecting the force required to move a plunger clip in reverse while restricting flow into the syringe. The apparatus and methods may also be used to determine that a syringe in the syringe pump apparatus is properly connected to a delivery line.

18 Claims, 3 Drawing Sheets

(56) References Cited

U.S. PATENT DOCUMENTS

| | | |
|---|---|---|
| 5,545,140 A | 8/1996 | Conero |
| 5,827,223 A | 10/1998 | Butterfield |
| 6,179,569 B1 | 1/2001 | Kojima |
| 6,200,289 B1 | 3/2001 | Hochman |
| 6,254,569 B1 | 7/2001 | O'Donnell |
| 6,423,035 B1 | 7/2002 | Das |
| 6,555,986 B2 | 4/2003 | Moberg |
| 6,575,936 B1 | 6/2003 | Kojima |
| 6,656,148 B2 | 12/2003 | Das et al. |
| 6,659,980 B2 | 12/2003 | Moberg |
| 7,087,033 B2 | 8/2006 | Brugger |
| 7,193,521 B2 | 3/2007 | Moberg |
| 7,517,332 B2 | 4/2009 | Tonelli |
| 7,758,547 B2 | 7/2010 | Tonelli |
| 8,011,250 B2 | 9/2011 | Trieu |
| 8,062,513 B2 | 11/2011 | Yu |
| 8,226,597 B2 | 7/2012 | Jacobson |
| 8,257,582 B2 | 9/2012 | Yu |
| 8,394,046 B2 | 3/2013 | Nuernberger |
| 8,485,998 B2 | 7/2013 | Moll |
| 8,512,554 B2 | 8/2013 | Yu |
| 8,715,215 B2 | 5/2014 | Kopperschmidt |
| 9,022,981 B2 | 5/2015 | Oesterreich |
| 9,352,083 B2 | 5/2016 | Heitmeier |
| 9,675,745 B2 | 6/2017 | Kelly |
| 9,731,068 B2 | 8/2017 | Rochette |
| 9,770,553 B2 | 9/2017 | Bazargan |
| 9,995,190 B2 | 6/2018 | Levorsen |
| 10,004,837 B2 | 6/2018 | Gronau |
| 10,071,200 B2 | 9/2018 | Alderete |
| 2003/0229311 A1 | 12/2003 | Morris |
| 2004/0152979 A1 | 8/2004 | Sakakibara |
| 2005/0220639 A1 | 10/2005 | Sasaki |
| 2007/0100281 A1 | 5/2007 | Morris |
| 2008/0161751 A1 | 7/2008 | Plahey |
| 2010/0256561 A1 | 10/2010 | Gillespie, Jr. |
| 2011/0077586 A1 | 3/2011 | Plahey |
| 2011/0190693 A1 | 8/2011 | Takatsuka |
| 2012/0234099 A1 | 9/2012 | Rochette |
| 2013/0281965 A1 | 10/2013 | Kamen |
| 2014/0188076 A1 | 7/2014 | Kamen |
| 2015/0094665 A1 | 4/2015 | Heitmeiter |
| 2015/0374902 A1 | 12/2015 | Chambers |
| 2016/0000996 A1 | 1/2016 | Faulhaber |
| 2017/0189608 A1 | 7/2017 | Stultz |
| 2017/0274141 A1 | 9/2017 | Stewart |
| 2017/0333623 A1 | 11/2017 | Kamen |

FOREIGN PATENT DOCUMENTS

| | | |
|---|---|---|
| EP | 1588729 | 10/2005 |
| EP | 1847285 | 10/2007 |
| EP | 1765436 B1 | 6/2009 |
| EP | 1938849 B1 | 3/2013 |
| EP | 2686039 | 1/2015 |
| EP | 2150293 | 2/2015 |
| EP | 2910264 | 8/2015 |
| EP | 2976116 B1 | 7/2017 |
| EP | 3222307 A1 | 9/2017 |
| EP | 2187992 B1 | 1/2018 |
| GB | 2356349 | 5/2001 |
| WO | WO 01/72357 | 10/2001 |
| WO | WO 2004053768 A2 | 6/2004 |
| WO | WO 2005/102418 | 11/2005 |
| WO | WO 2012/126744 | 9/2012 |
| WO | WO 2015/062926 | 5/2015 |
| WO | WO 2017060166 A1 | 4/2017 |
| WO | WO 2017108686 A1 | 6/2017 |
| WO | WO 2017116953 A1 | 7/2017 |
| WO | WO 2018033490 A1 | 2/2018 |
| WO | WO 2018036875 A1 | 3/2018 |

OTHER PUBLICATIONS

PCT International Preliminary Report on Patentability for PCT/US2013/077926 dated Jul. 9, 2015 (9 pages).

SYRINGE PUMP ENGAGEMENT DETECTION APPARATUS AND METHODS

CROSS-REFERENCE

This application is a divisional of U.S. patent application Ser. No. 13/655,245, filed Jun. 24, 2015, which is a U.S. National Stage Application of International Application No. PCT/US2013/077926, filed Dec. 27, 2013 and published in English on Jul. 3, 2014 as International Publication No. WO 2014/106008 A1, which claims the benefit under 35 U.S.C. 119(e) of U.S. Provisional Application No. 61/746,697, filed Dec. 28, 2012, the disclosure of which are incorporated herein by reference in their entirety.

Apparatus and methods for detecting proper engagement of a drive system with a syringe in a syringe pump are described herein.

BACKGROUND

Syringe pumps are used in many different apparatus to deliver or remove fluids using a syringe by moving a plunger within a syringe barrel. Examples of some potential apparatus that may use a syringe pump include, but are not limited to, infusion pumps used to deliver a substance using a syringe, extracorporeal blood treatment devices, etc.

Extracorporeal blood treatment involves taking the blood from a patient, treating the blood outside the patient, and returning the treated blood to the patient. Extracorporeal blood treatment may be used to extract undesirable matter or molecules from the patient's blood and/or to add one or more beneficial substances to the blood. In many extracorporeal blood treatment devices in which one or more beneficial substances are introduced in liquid form into blood being treated extracorporeally, the liquids are delivered using a syringe pump. One example of a beneficial substance delivered in liquid form using a syringe pump in an extracorporeal blood treatment device is an anticoagulant (e.g., heparin).

Conventional syringe pumps, including those used in extracorporeal blood treatment devices, typically include apparatus and controls needed to dispense material from the syringe, without concern for whether or not the syringe is completely secured in the syringe pump. In particular, conventional syringe pump control systems are designed to detect occlusions that may impede or prevent accurate delivery of the beneficial substance in the syringe.

SUMMARY

Syringe pump engagement detection apparatus and methods as described herein can be used to detect proper or improper engagement of a syringe pump drive system with a syringe in the syringe pump. In particular, the apparatus and methods described herein can determine proper or improper engagement between a drive system and the plunger of a syringe in a syringe pump by detecting the force required to move a plunger clip while restricting flow into and/or out of the syringe barrel.

One potential advantage of the apparatus and/or methods described herein is to reduce the likelihood that the contents of a syringe in a syringe pump are inadvertently emptied into a fluid line connected to the syringe. For example, in some instances, the contents of a syringe in a syringe pump may be emptied into a fluid line connected to the output of the syringe pump if the pressure in an output line connected to the outlet of a syringe reaches a negative pressure (i.e., a vacuum) high enough to overcome the force required to advance the plunger tip through the barrel of the syringe. This phenomenon is sometimes referred to as "siphoning" of the contents in the syringe.

To prevent this from occurring, a plunger clip may be engaged with the plunger to prevent unwanted movement of the plunger relative to the plunger clip. One example of a plunger clip designed to address siphoning in connection with a syringe pump is described in U.S. Pat. No. 5,254,096 (Rondelet et al.). That approach, however, focuses on monitoring the structure used to capture the plunger directly to determine if the structure is closed, regardless of whether or not the plunger is actually captured in the device.

To detect proper or improper engagement of the plunger clip with the plunger of the syringe, the syringe pump apparatus described herein determines whether or not the plunger clip is properly engaged by moving the plunger clip in reverse while monitoring the force required to move the plunger clip. If the plunger clip is properly engaged with the syringe plunger, the force required to move the plunger clip reaches or exceeds a selected force level because fluid is restricted from flowing into the syringe, thus resulting in a negative pressure in the syringe. If the plunger clip is not properly engaged, the force required to move the plunger clip in reverse will not reach the selected force level because the plunger clip will not move the plunger and negative pressure will not be developed in the syringe.

Moving the plunger of a syringe in a syringe pump apparatus as described herein could, in some instances, pull air into the syringe or the delivery line to which the syringe is attached. If the contents of the syringe are intended for delivery into a patient, either directly into the patient's vasculature or into a line, e.g., a blood line connected to the patient's vasculature, the inclusion of air in the liquid delivered from the syringe may be problematic. The syringe pump apparatus described herein may, in one or more embodiments where air in the syringe and/or delivery line may be problematic, deliver the syringe contents to one or more components downstream from the syringe that are designed to remove air and/or detect the air and stop its movement through the system to reduce the likelihood that any such air is delivered with the liquid in the syringe. Components used to remove and/or detect air in liquid lines may include, e.g., bubble traps, air detectors and clamps, etc.

Another potential benefit of syringe pump engagement detection apparatus and methods described herein is that in one or more embodiments, the force sensor used to determine proper or improper engagement of the plunger clip with the syringe is the same force sensor used to detect an occlusion in the delivery line through which fluids are delivered from a syringe in the syringe pump. This may reduce the cost and/or complexity of the apparatus as compared to an apparatus requiring an additional sensor to detect capture of syringe plunger.

In one or more embodiments, the syringe pump apparatus and methods described herein may also provide opportunities to determine if the syringe in a syringe pump apparatus is properly connected to a delivery line.

In one or more embodiments, a syringe pump apparatus configured to detect engagement between a drive system and a plunger of a syringe in the syringe pump apparatus as described herein may include: a syringe retainer configured to retain a syringe in a fixed position in the syringe pump apparatus; a flow control device configured to prevent flow into a syringe retained in the syringe retainer; a plunger clip configured to capture a plunger of a syringe retained in the syringe retainer; a drive system configured to move the plunger clip relative to the syringe retainer; and a force sensor configured to measure a force exerted on the plunger clip by the drive system. The apparatus may further include a control unit operably connected to the drive system and the force sensor, wherein the control unit is configured to: move the plunger clip away from the syringe retainer using the drive system; measure the force exerted on the plunger clip by the drive system using the force sensor; and make a determination that the plunger clip is properly engaged with a plunger of a syringe retained in the syringe retainer if the force measured by the force sensor reaches or exceeds a selected force level while the flow control device prevents flow into the syringe.

In one or more embodiments of the syringe pump apparatus described herein, the control unit is configured to make a determination that the plunger clip is not properly engaged with a plunger of a syringe in the syringe retainer if the force measured by the force sensor has not reached the selected force level after the drive system has moved the plunger clip a selected limit distance.

In one or more embodiments of the syringe pump apparatus described herein, the selected force level is dependent on a distance over which the drive system has moved the plunger clip, wherein the selected force level increases as the distance increases.

In one or more embodiments of the syringe pump apparatus described herein, the control unit is configured to stop the drive system from moving the plunger clip away from the syringe retainer when the selected force level is reached.

In one or more embodiments of the syringe pump apparatus described herein, the control unit is configured to measure the force exerted on the plunger clip by the drive system while the drive system is moving the plunger clip.

In one or more embodiments of the syringe pump apparatus described herein, the control unit is configured to stop the drive system from moving the plunger clip away from the syringe retainer when the drive system has moved the plunger clip over a selected limit distance.

In one or more embodiments of the syringe pump apparatus described herein, the flow control device is configured to selectively close to prevent flow into a syringe retained in the syringe retainer, wherein the flow control device is operably connected to the control unit which is configured to selectively close the flow control device before the plunger clip is moved away from the syringe retainer by the drive system. In one or more embodiments, the flow control device is normally open. In one or more embodiments, the control unit is configured to move the plunger clip forward toward the syringe retainer using the drive system, and wherein the flow control device is normally open when the plunger clip is moving forward toward the syringe retainer. In one or more embodiments, the flow control device comprises a clamp or a valve.

In one or more embodiments of the syringe pump apparatus described herein, the flow control device is configured to selectively prevent flow out of the syringe, and wherein the control unit is configured to: close the flow control device to prevent flow out of the syringe; move the plunger clip toward the syringe retainer using the drive system while the flow control device is closed; measure the force exerted on the plunger clip by the drive system using the force sensor; and make a determination that a syringe is properly connected to a delivery line if the force measured by the force sensor while moving the plunger clip towards the syringe retainer reaches or exceeds a selected delivery force level.

In one or more embodiments of the syringe pump apparatus described herein, an air control apparatus is positioned downstream from an outlet of a syringe in the syringe retainer.

In one or more embodiments of the methods of detecting engagement between a drive system and a plunger of a syringe in a syringe pump as described herein, the methods may include: moving a plunger clip away from a syringe retainer configured to retain a syringe in a fixed position; preventing flow into the syringe in the syringe retainer while moving the plunger clip away from the syringe retainer; measuring a force exerted on the plunger clip while preventing flow into the syringe; and determining that the plunger clip is properly engaged with the plunger of the syringe in the syringe retainer if the measured force reaches or exceeds a selected force level.

In one or more embodiments of the methods described herein, the method comprises determining that the plunger clip is not properly engaged with the plunger if the measured force has not reached the selected force level after moving the plunger clip a selected limit distance.

In one or more embodiments of the methods described herein, the selected force level is dependent on a distance over which the plunger clip moves, and wherein the selected force level increases as the distance increases.

In one or more embodiments of the methods described herein, the method comprises stopping movement of the plunger clip away from the syringe retainer when the selected force level is reached.

In one or more embodiments of the methods described herein, the method comprises measuring the force exerted on the plunger clip while moving the plunger clip.

In one or more embodiments of the methods described herein, preventing flow into the syringe comprises closing a flow control device. In one or more embodiments, the method comprises closing the flow control device before moving the plunger clip away from the syringe retainer.

In one or more embodiments of the methods described herein, the method comprises moving the plunger clip toward the syringe retainer to a selected position after determining that the plunger clip is properly engaged with the plunger of the syringe in the syringe retainer. In one or more embodiments, the selected position comprises a starting position of the plunger clip, wherein the starting position comprises a position of the plunger clip before moving the plunger clip away from the syringe retainer.

In one or more embodiments of the methods described herein, the method comprises: moving the plunger clip toward the syringe retainer while preventing flow out of the syringe; measuring the force exerted on the plunger clip by the drive system using the force sensor while moving the plunger clip toward the syringe retainer and preventing flow out of the syringe; and determining that the syringe is properly connected to a delivery line if the force measured by the force sensor while moving the plunger clip towards the syringe retainer reaches or exceeds a selected delivery force level.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the syringe pump engagement detection apparatus and methods described herein. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Although illustrative embodiments of the syringe pump apparatus and methods are described herein in the context of an extracorporeal blood treatment device, the syringe pump engagement detection apparatus and methods described herein may be used in any other suitable device that includes a syringe pump such as, e.g., infusion pumps, etc.

Figure 1:
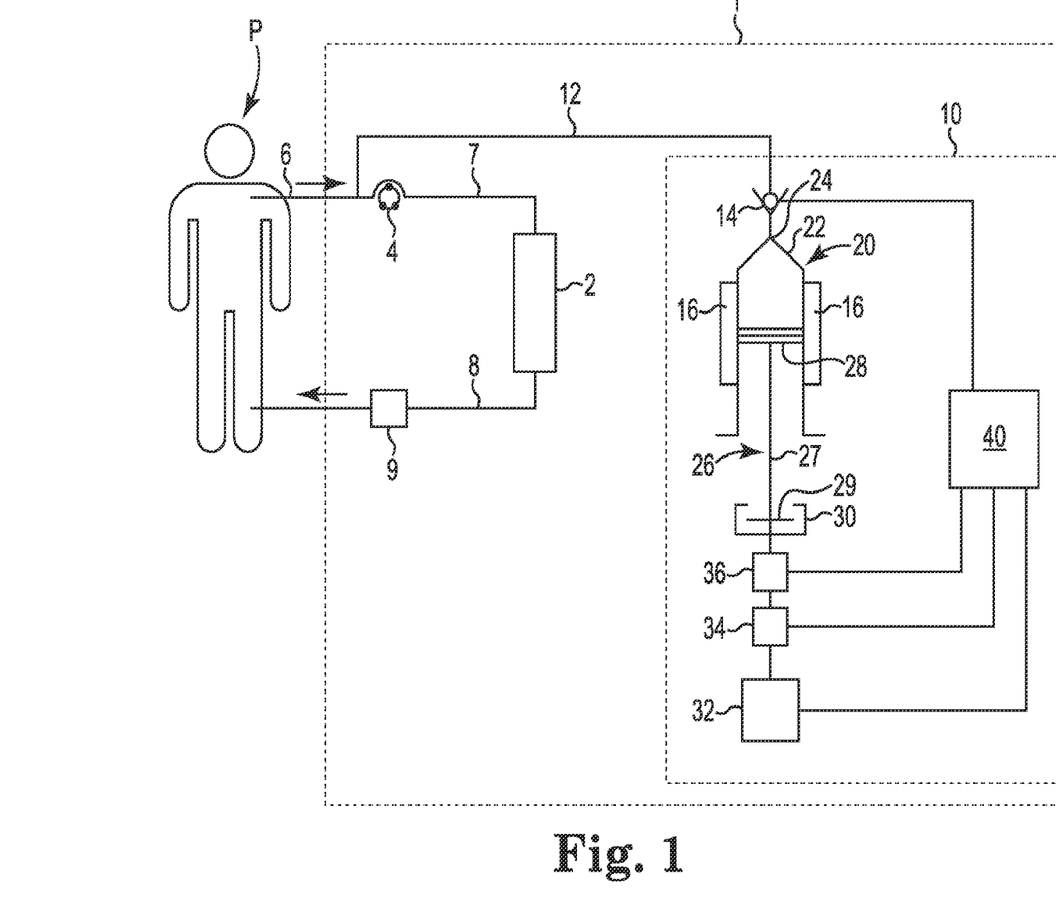
FIG. 1 is a schematic depiction of one illustrative embodiment of a syringe pump apparatus as described herein provided in connection with an extracorporeal blood treatment device.

Referring to FIG. 1, one illustrative embodiment of a syringe pump apparatus 10 configured to detect engagement between a drive system and a plunger of a syringe in the syringe pump apparatus 10 is depicted in connection with a simplified diagram of one illustrative embodiment of an extracorporeal blood treatment device 1. The depicted extracorporeal blood treatment device 1 may, for example, be configured to perform one or more of the following treatments: hemodialysis, pure ultrafiltration, hemofiltration, hemodiafiltration, therapeutic plasma exchange, etc.

The extracorporeal blood treatment device 1 depicted schematically in FIG. 1 may be used for, e.g., treatment of kidney failure using a filter 2 that is operatively associated with a blood circuit that includes an arterial line 6 through which blood is removed from a patient P and delivered to the filter 2 using, e.g., a blood pump 4. The blood circuit also includes a venous line 8 used to return blood to the patient P from the filter 2.

In the depicted embodiment, an air control apparatus 9 is located in the venous line 8 to remove and/or detect air in the liquid (primarily blood) passing through the venous line 8. The air control apparatus 9 may take a variety of different forms including one or more of the following components: a bubble trap used to remove air entrained in a liquid, an air detector used to detect air in a liquid along with a clamp, valve, etc. that can be used to close the venous line 8 to reduce the likelihood that air in the venous line 8 reaches the patient P. Although not depicted in FIG. 1, the air control apparatus 9 may be operably connected with the control unit 40, which may, in one or more embodiments, be configured to stop the flow of all liquid through the air control apparatus 9 if air is detected in the liquid.

The extracorporeal blood treatment device 1 also includes one illustrative embodiment of a syringe pump apparatus 10 as described herein that can be used to deliver one or more medical liquids (e.g., substitution liquids, anticoagulant, etc.) to one or more locations in the extracorporeal blood treatment device 1. For example, if the syringe pump apparatus 10 is used to deliver a liquid anticoagulant, the syringe pump apparatus 10 will typically include a delivery line 12 connected to the arterial line 6 extracorporeal blood treatment device 1 so that anticoagulant (or any other selected liquid) can be delivered to blood in the arterial line 6. In one or more alternative embodiments, the syringe pump apparatus 10 may be connected to deliver liquid from a syringe to any suitable location in the extracorporeal blood treatment device 1 other than the arterial line 6 (such as, e.g., the venous return line 8, the pre-filter line 7, etc.). In another variation, for example, the delivery line 12 of the syringe pump apparatus 10 may be configured to deliver liquid directly to the patient P.

The syringe pump apparatus 10 depicted schematically in FIG. 1 is configured to dispense liquid from a syringe 20 retained in the syringe pump apparatus 10 into the delivery line 12. Typically, the syringes 20 used in connection with the syringe pump apparatus 10 are of a single-use type, such that after use they are discarded, although in one or more embodiments, a syringe may be re-used.

The syringe 20 for which the syringe pump apparatus 10 is designed typically includes a syringe barrel 22, an outlet 24, and a plunger 26 that includes a stem 27 connecting a seal 28 to the plunger base 29 with the seal 28 residing in the barrel 22. Liquid contained in the barrel 22 exits the syringe 20 through the outlet 24 as the seal 28 of the plunger 26 is advanced towards the outlet 24.

The syringe pump apparatus 10 depicted in FIG. 1 includes a syringe retainer 16 that is configured to retain a syringe 20 in a fixed position in the syringe pump apparatus 10. In one embodiment as depicted in FIG. 1, the syringe retainer 16 may be in the form of a clamp designed to hold the syringe barrel 22. Syringe retainers used in the syringe pump apparatus described herein may, however, take many other forms including any structure capable of retaining a syringe in a fixed position as needed for proper operation of the syringe pump apparatus described herein.

Another component of the syringe pump apparatus 10 depicted in FIG. 1 is a flow control device 14 that configured to prevent flow into the syringe 20 retained in the syringe retainer 16 of the syringe pump apparatus 10. In particular, the flow control device 14 is configured to prevent flow into the barrel 22 of the syringe 20. Although the flow control device 14 is described as preventing flow into the syringe 20, as used herein "prevent" (and variations thereof) as used to describe complete occlusion (such that no flow is allowed) or flow restriction that is great enough to provide a negative pressure in the syringe as described herein that, in turn, results in a force required to move the plunger 26 large enough to make a determination that a plunger clip 30 (described in more detail herein) is properly engaged with the plunger 26 of the syringe 20 retained in the syringe retainer 16 (i.e., complete occlusion may not be required).

In one or more embodiments, the flow control device 14 may be located anywhere along the delivery line 12. In one or more alternative embodiments, the flow control device 14 may be located at the outlet 24 of the syringe 20 such that, e.g., the flow control device 14 is located between the delivery line 12 and the interior volume of the syringe barrel 22.

In one or more embodiments, the flow control device 14 may be configured to selectively close to prevent flow into the syringe 20 retained in the syringe retainer 16. For example, the flow control device 14 may be in the form of a valve or a clamp that can be selectively closed by an operator or a control unit 40 (described in more detail herein). If the flow control device 14 is provided in the form of a valve, clamp, etc. that must be selectively closed, the flow control device 14 may be normally open such that, in the absence of selective closure, the flow control device 14 is open to allow flow therethrough. In one or more alternative embodiments, the flow control device 14 may be in the form of one-way valve such that flow out of the syringe 20 is allowed (when, e.g., the plunger is advanced in the forward direction), but reverse flow, i.e., flow into the syringe 20 is prevented without any action by, e.g., an operator, a control unit, etc. In one or more embodiments in which the flow control device 14 is a valve, it may be a pressure release one way valve.

The control units used in the syringe pump apparatus described herein may be provided in any suitable form and may, for example, include memory and a controller. The controller may, for example, be in the form of one or more microprocessors, Field-Programmable Gate Arrays (FPGA), Digital Signal Processors (DSP), microcontrollers, Application Specific Integrated Circuit (ASIC) state machines, etc. The control units may include one or more of any suitable input devices configured to allow a user to operate the apparatus (e.g., keyboards, touchscreens, mice, trackballs, etc.), as well as display devices configured to convey information to a user (e.g., monitors (which may or may not be touchscreens), indicator lights, etc.).

The illustrative embodiment of the syringe pump apparatus 10 described herein, as depicted in FIG. 1, also includes a plunger clip 30, a drive system 32 configured to move the plunger clip 30 relative to the syringe retainer 16 (in which the syringe 20 is retained), a force sensor 34 configured to measure the force exerted on the plunger clip 30 by the drive system 32, and a control unit 40 operably connected to the drive system 32 and the force sensor 34. The illustrative embodiment of the syringe pump apparatus 10 depicted in FIG. 1 also includes an optional displacement sensor 36 configured to determine the distance over which the drive system 32 moves the plunger clip 30 during operation of the syringe pump apparatus 10. Although the optional displacement sensor 36 of the syringe pump apparatus 10 of FIG. 1 is depicted as a separate component, in one or more embodiments the displacement sensor 36 may be integrated into the drive system 32.

The plunger clip 30 is configured to capture the plunger 26 of the syringe 20 retained in the syringe retainer 16. In the embodiment depicted in FIG. 1, the plunger clip 30 is configured to capture the plunger base 29, although in one or more alternative embodiments, the plunger clip 30 may capture any portion of the plunger 26, so long as the drive system 32 is capable of moving the plunger 26 using the plunger clip 30 over the needed distance.

The control unit 40 is configured to move the plunger clip 30 relative to the syringe retainer 16 using the drive system 32. The control unit 40 (using drive system 32) is, in one or more embodiments, configured to move the plunger clip 30 both towards and away from the syringe retainer 16 using the drive system 32. In particular, the control unit 40 (using drive system 32) is configured to move the plunger clip 30 away from the syringe retainer 16 (which direction will be referred to as reverse); measure the force exerted on the plunger clip 30 by the drive system 32 using the force sensor 34; and make a determination that the plunger clip 30 is properly engaged with the plunger 26 of the syringe 20 retained in the syringe retainer 16 if the force measured by the force sensor 34 reaches or exceeds a selected force level while the flow control device 14 prevents flow into the syringe 20. In addition, the control unit 40 (using drive system 32) will, in one or more embodiments, typically be configured to terminate movement of the drive system 32 in reverse when the force measured by the force sensor 34 reaches or exceeds the selected force level.

The force applied by the drive system 32 on the plunger clip 30 will reach the selected force level when the flow control device 14 prevents flow into the syringe 20 because movement of the plunger clip 30 in reverse by the drive system 32 will result in a negative pressure in the syringe 20. That negative pressure will require the drive system 32 to exert a larger force because it will become increasingly harder to move the plunger clip 30 as the pressure in the syringe 20 drops. The negative pressure is caused by increasing the enclosed volume within the syringe barrel 22 as the plunger seal 28 is moved in reverse and the flow control device 14 is closed to prevent additional fluid from entering the syringe 20.

The selected force level at which a determination can be made that the plunger clip 30 is properly engaged with a syringe plunger 26 will vary depending on the size of the syringe 20, the location of the flow control device 14 relative to the outlet 24 of the syringe 20, and a variety of other factors.

In one or more embodiments in which the flow control device 14 is of a type in which the flow control device 14 must be selectively closed to prevent flow into the syringe 20, the control unit 40 is configured to selectively close the flow control device 14 before or while the plunger clip 30 is moved away from the syringe retainer 16 by the drive system 32. Although it may be advantageous to close the flow control device 14 in such a system before moving the plunger clip 30 in reverse, the system may operate even if the flow control device 14 is closed after the drive system 32 has started to move the plunger clip 30 in reverse. In one or more embodiments in which the flow control device 14 does not need to be selectively closed, this function is not required of the control unit 40. For example, if the flow control device 14 is a one way check valve, the control unit does not need to selectively close the flow control device 14.

Because the drive system 32 of the syringe pump apparatus 10 described herein needs to move the plunger 26 in the reverse direction, the plunger clip 30 must engage the plunger 26 in a way that is capable of moving the plunger 26 in the reverse direction. In other words, unlike many conventional syringe pumps, the syringe pump apparatus 10 must include a plunger clip 30 that is capable of not only pushing or moving the plunger 26 in the forward direction to dispense material from a syringe, but it must also be able to pull or move the plunger 26 in the reverse direction. In one or more embodiments, the plunger clip may include a slot into which the plunger base 29 can be inserted, clamps that provide the desired connection between the plunger clip 30 and the plunger 26, or any other suitable structure capable of moving the plunger of syringe in the reverse direction (one potential example of which is described in U.S. Pat. No. 5,254,096 (Rondelet et al.)).

In one or more embodiments, the control unit 40 is configured to make a determination that the plunger clip 30 is not properly engaged with the plunger 26 of a syringe 20 in the syringe retainer 16 if the force measured by the force sensor 34 has not reached the selected force level after the drive system 32 has moved the plunger clip 30 a selected limit distance. In such a situation, where the plunger clip 30 has moved the selected limited distance and the selected force level has not been detected by the force sensor 34, a determination can be made that the plunger clip 30 is not engaged with the plunger 26 because movement of the plunger 26 in reverse would otherwise result in a negative pressure within the syringe 20. Failure to reach that negative pressure and the resulting selected force level are indicative of a failure of the plunger clip 32 properly engaged with the plunger 26. In the illustrative embodiment of the syringe pump apparatus 10 depicted in FIG. 1, the distance over which the plunger clip 30 travels may be measured using a displacement sensor 36.

In one or more embodiments, the selected force level at which a determination can be made that the plunger clip 30 is not properly engaged with the plunger 26 of a syringe in the syringe retainer 16 may be dependent on a distance over which the drive system 32 has moved the plunger clip 30 (and the plunger 26 if properly engaged with the plunger clip 30). In such a situation, the selected force level typically increases as the distance over which the plunger clip 30 is moved in reverse increases. In one or more embodiments, the control unit 40 may be configured to make a determination that the plunger clip 30 is not properly engaged with the plunger 26 of a syringe in the syringe retainer 16 based on a combination of the force detected by the force sensor 34 and the distance over which the plunger clip 30 has moved as measured by the displacement sensor 36. In one or more embodiments, the control unit 40 may be configured to measure the force exerted on the plunger clip 30 by the drive system 32 while the drive system 32 is moving the plunger clip 30 and, based on a combination of the force as measured by the force sensor 34 and the distance over which the plunger clip 30 has moved as measured by the displacement sensor 36, make a determination that the plunger clip 30 is or is not properly engaged with the plunger 26 of a syringe 20 in the syringe retainer 16.

In one or more embodiments, the control unit 40 may also be configured to terminate movement of the plunger clip 30 in the reverse direction by the drive system 32 after the plunger clip 30 has moved over a selected distance as determined by the displacement sensor 36 while the force sensor 34 has not indicated that the selected force level has been reached. In such a situation, the control unit 40 can make that determination because failure to reach the selected force level occurs because the plunger 26 is not being moved in the reverse direction by the plunger clip 30 and, therefore, a negative pressure is not being obtained in the syringe 20.

In one or more embodiments, the control unit 40 may also be configured to terminate movement of the plunger clip 30 in the reverse direction by the drive system 32 after the plunger clip 30 has moved over a selected distance as determined by the displacement sensor 36 regardless of the signals received from the force sensor 34.

In one or more embodiments, the apparatus and methods described herein may also involve moving the plunger clip 30 forward (toward the syringe retainer 16) to a selected location (e.g., the original starting position of the plunger clip 30, etc.) after having moved the plunger clip 30 in reverse to detect proper or improper engagement of a plunger clip 30 with a plunger of a syringe 20. For example, a control unit 40 may be configured to operate the drive system 32 to accomplish these actions.

Although the air control apparatus 9 in the embodiment of the extracorporeal blood treatment device 1 depicted in FIG. 1 is located fairly remote from the syringe pump apparatus 10, it is downstream from the outlet 24 of a syringe 20 retained in the syringe pump apparatus 10 because liquid delivered from the syringe 20 into the delivery line 12 enters the extracorporeal blood treatment device 1 through the arterial line 6 as described herein. The liquid (and any air entrained therein) would, before reaching the patient P, pass through the air control apparatus 9 where the air could be removed and/or its advancement could be stopped.

In one or more alternative embodiments, an air control apparatus 9 could be located downstream from the outlet of a syringe 20 in the syringe pump apparatus 1 by being incorporated into the delivery line 12 itself or an air control apparatus 9 could be provided between the outlet 24 of the syringe 20 and the delivery line 12 to stop advancement of entrained air. Many other locations for the air control apparatus 9 may also exist and be effective so long as they are downstream from the outlet 24 of the syringe 20 and upstream from the point where liquid from the syringe 20 enters the patient P. In one or more embodiments, the air control apparatus 9 may be located downstream from the flow control device 14 described herein.

Figure 2:
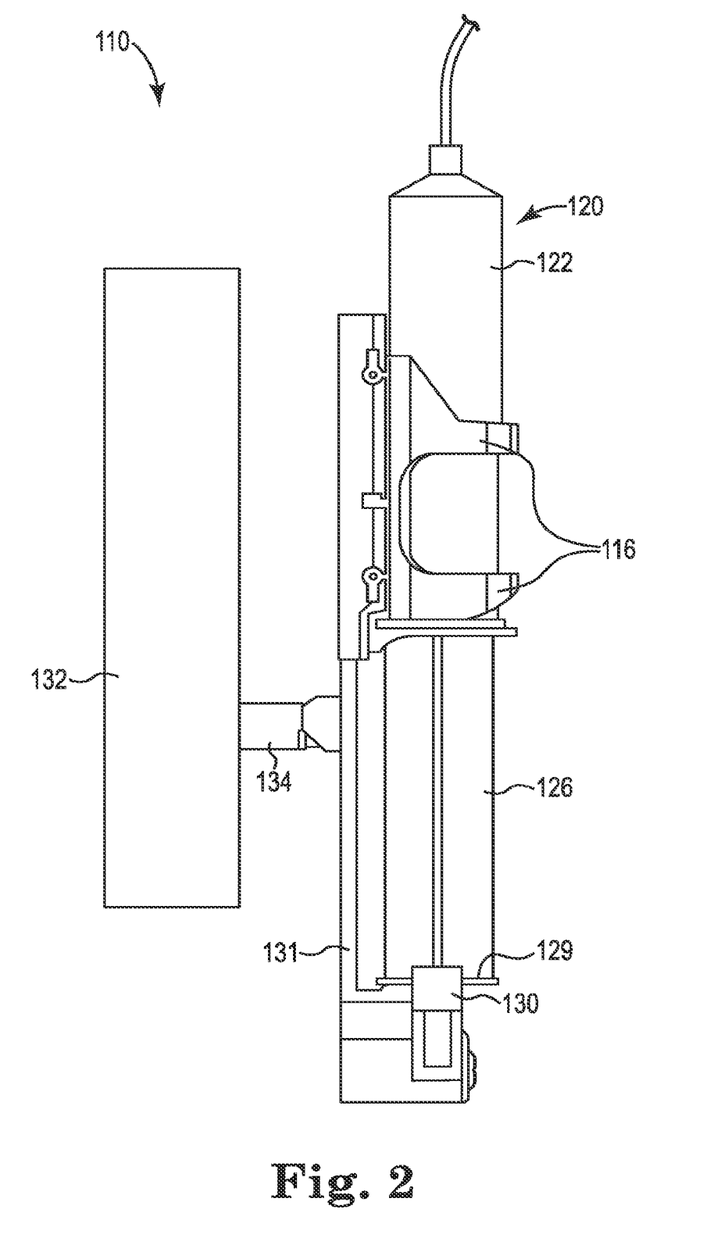
FIG. 2 depicts one illustrative embodiment of a syringe pump apparatus as described herein.

One illustrative embodiment of syringe pump apparatus 110 is depicted in FIG. 2. The syringe pump apparatus 110 includes a syringe retainer 116 in the form of clips which receive a barrel 122 of a syringe 120. The syringe pump apparatus 110 also includes a plunger clip 130 mounted on a truck 131 which is driven by a drive system 132 as described herein. The plunger clip 130 is capable of capturing the plunger base 129 of the plunger 126 of the syringe 120 to move the plunger 126 in both the forward direction (towards the syringe retainer 116) and the reverse direction (away from the syringe retainer 116). The syringe pump apparatus 110 also includes a force sensor 134 capable of detecting the force exerted on the truck 131 and, thereby, on the plunger clip 130. The force sensor 134 may, in one or more embodiments, be a bidirectional force sensor such that it can detect the forces exerted on the truck 131 as the plunger clip 130 is moved in both the forward and reverse directions. At a minimum, however, the force sensor 134 is configured to determine the force exerted on the truck 131 by the drive system 132 when the plunger clip 130 is being moved in the reverse direction.

The drive systems used in the apparatus and/or methods described herein may be in a variety of forms so long as they are capable of moving the plunger clips as described herein. For example, in one or more embodiments, the drive system may include a lead screw operably connected to a motor. The connection between the motor and the lead screw may be direct (i.e., the lead screw may be coupled directly to an output shaft of the motor) or the motor may be coupled to the lead screw using one or more intermediate components such as, e.g., a gear, belt, etc. The motors used may be of any suitable type, e.g., brushed, brushless, stepper motor, etc.

The displacement sensors used in the apparatus and/or methods described herein may be in a variety of forms so long as they are capable of measuring displacement of the plunger clips as described herein. For example, in one or more embodiments, the displacement sensors may be in the form of encoders, proximity sensors, photodetectors, etc. In one or more embodiments, the displacement sensor may be in the form of an encoder attached to the motor of the drive system, with independent reference positions at the start and the end of travel to determine the distance traveled by the plunger clips in the apparatus and methods described herein.

In one or more alternative embodiments, the displacement sensor may be integral with the drive system, e.g., if the drive system uses a stepper motor, the displacement of the plunger clip may be determined based on the number of pulses delivered to the stepper motor (e.g., the pulses may be summed to determine the displacement distance based on estimates of the distance traveled by the plunger clip with each pulse delivered to the stepper motor).

The force sensors used in the apparatus and/or methods described herein may be in a variety of forms so long as they are capable of measuring the force exerted on the plunger clips as described herein. For example, in one or more embodiments, the force sensors may be in the form of a strain gauge (e.g., a resistive, capacitive or piezo-electric strain gauge). In one or more alternative embodiments, the force sensor could be in the form of a spring switch that is opened or closed when the selected force level is reached as described herein.

Figure 3:
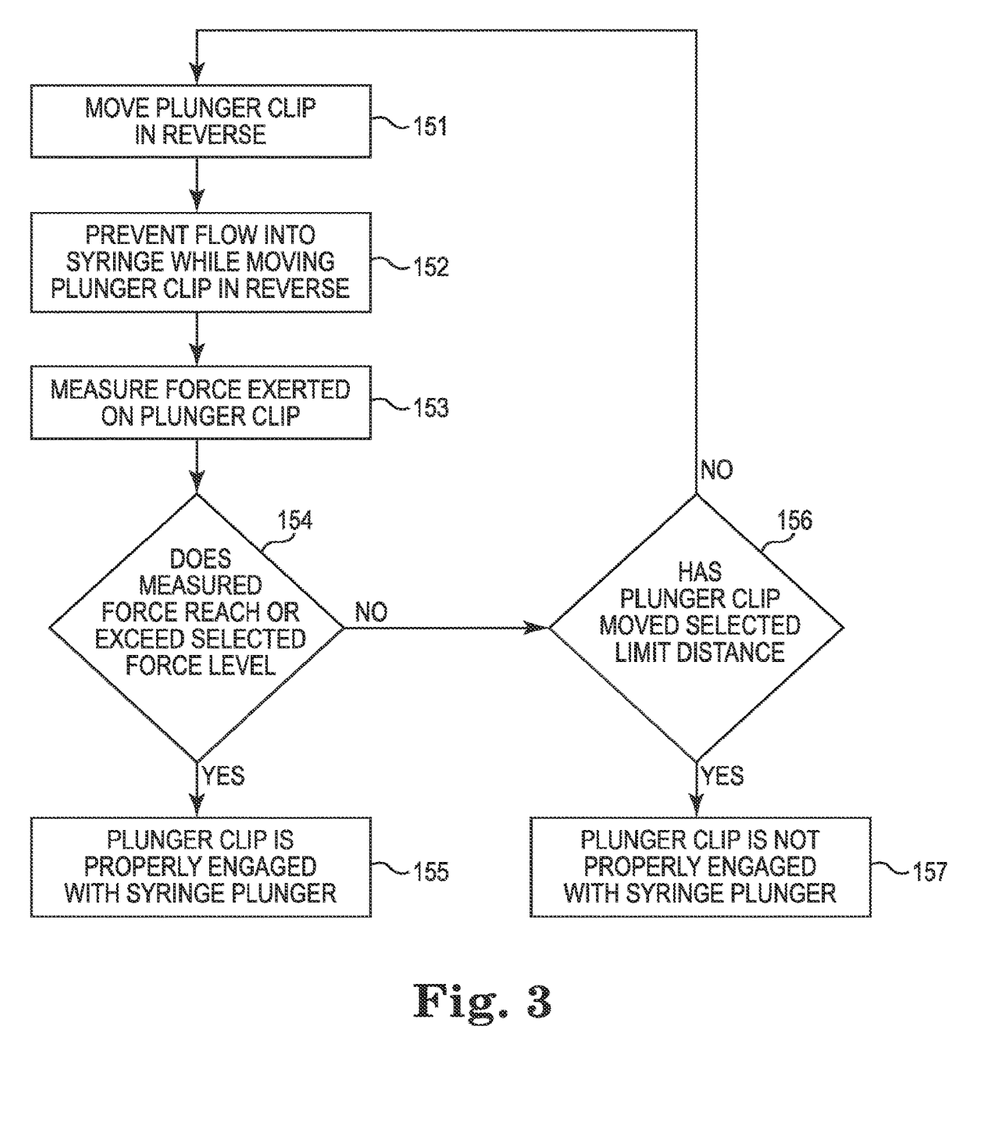
FIG. 3 is a flowchart depicting one illustrative embodiment of a method as described herein.

Although methods of detecting engagement between a drive system and a plunger of a syringe in a syringe pump apparatus are described in connection with the apparatus depicted in FIG. 1, one or more embodiments of the methods of detecting engagement between a drive system and a plunger of a syringe in a syringe pump apparatus as described herein may include the steps depicted in the flowchart of FIG. 3. The illustrative embodiment of the method depicted in the flowchart of FIG. 3 includes moving a plunger clip in reverse 151, e.g., moving the plunger clip of a syringe pump apparatus away from a syringe retainer configured to retain a syringe in a fixed position. The method further includes preventing flow into the syringe 152 while moving the plunger clip away from the syringe retainer in which the syringe is located. The force exerted on the plunger clip is measured 153 while preventing flow into the syringe and moving the plunger clip away from the syringe retainer. If the force exerted on the plunger clip while moving the plunger clip away from the syringe retainer reaches or exceeds a selected force level 154, then a determination is made that the plunger clip is properly engaged with the plunger of the syringe in the syringe retainer 155. In one or more embodiments, the method may include stopping movement of the plunger clip away from the syringe retainer when the selected force level is reached.

The method may further include measuring the distance over which the plunger clip has traveled to determine if a selected limit distance has been reached 156. The method may further include making a determination that the plunger clip is not properly engaged with the plunger if the measured force has not reached or exceeded the selected force level when the plunger clip has traveled over a selected limit distance 157.

In one or more embodiments, the selected force level may be dependent on the distance over which the plunger clip moves. In such an arrangement, the selected force level at which a determination that the plunger clip is or is not properly engaged with a syringe plunger may increase as the distance over which the plunger clip has traveled increases.

In one or more embodiments of the apparatus and methods described herein, the force exerted on the plunger clip may be measured while moving the plunger clip. In one or more embodiments of the apparatus and methods described herein, the force exerted on the plunger clip may be measured while the plunger clip is in a stationary position after having been moved in the reverse direction, i.e., away from the syringe retainer.

In one or more embodiments of the methods described herein, the method may further include closing a flow control device, such as, e.g., a valve, clamp etc. In methods in which the flow control device is closed, the method may include selectively closing the flow control device before moving the plunger clip away from the syringe retainer. In one or more other embodiments, however, a flow control device which must be selectively closed may be closed after the plunger clip has begun to move away from the syringe retainer.

The addition of the flow control devices and force sensors in the syringe pump apparatus described herein may also provide opportunities in the replacement of a syringes in the syringe pumps. In one or more embodiments, a method of replacing a syringe in a syringe pump apparatus as described herein may include selectively closing the delivery line (using, e.g., the flow control device or another device, e.g., a clamp or valve if the flow control device is a one-way check valve), followed by disconnecting the delivery line from the outlet of the syringe in the syringe pump. In one or more embodiments, the drive system may be activated by the control unit to move the plunger clip in reverse (i.e., away from the syringe retainer) after the delivery line has been disconnected from the outlet of the syringe.

The syringe may, in one or more embodiments, be removed from the syringe retainer after the delivery line has been disconnected from the outlet of the syringe and, in those embodiments in which the plunger clip is moved in reverse, after the plunger clip has been moved in reverse. Removal of the syringe from the syringe retainer typically includes removing the plunger base from the plunger clip.

After the syringe has been removed from the syringe pump apparatus, a new syringe is placed in the syringe retainer and the delivery line is connected to the outlet of the new syringe. In one or more embodiments, the drive system is then activated by the control unit to move the plunger clip forward (i.e., toward the syringe retainer) so that the plunger clip acts against the plunger base. The delivery line is still closed (by, e.g., the flow control device or another device, e.g., a clamp or valve if the flow control device is a one-way check valve) during forward movement of the plunger clip and, as a result, the drive system exerts an increasing force on the plunger clip because fluid is not allowed to leave the syringe. The drive system may be de-activated after forward movement of the plunger clip by the drive system results in a force exerted on the plunger that exceeds a selected delivery force level. Reaching that selected delivery force level during forward movement of the plunger clip can, in one or more embodiments, be relied on as an indicator that the delivery line is properly connected to the outlet of the syringe. Conversely, a failure to reach the selected delivery force level may result in a determination that the delivery is not properly connected to the syringe outlet.

One or more embodiments of the methods described herein may further include engaging the plunger clip with the plunger (e.g., the plunger base). This action may be performed before or after the plunger clip drives the plunger in the forward direction. In one or more embodiments, the user may provide an indication to the a control unit of the syringe pump apparatus that the plunger clip has been engaged with the plunger (using any suitable input device, e.g., button, switch, touchscreen, touchpad, etc.).

After engaging the plunger clip with the plunger, the method may involve moving the plunger clip in reverse as described herein to determine whether or not the plunger clip has been properly engaged with the plunger of the new syringe.

In one or more embodiments of the methods described herein, the method may include moving the plunger clip toward the syringe retainer to a selected position after determining that the plunger clip is properly engaged with the plunger of the syringe in the syringe retainer. In one or more embodiments, the selected position of the plunger clip may be a starting position of the plunger clip, where the starting position was/is the position of the plunger clip before the plunger clip was moved away from the syringe retainer to determine if the plunger clip was properly engaged with a plunger of a syringe.

Following reversal of the plunger clip, one or more embodiments of the methods and apparatus described herein may include moving the plunger clip in the forward direction until a selected delivery force level is reached as measured by a force sensor and/or until the plunger clip is at its original starting position. The selected delivery force level may correspond, for example, to fluid pressure in the syringe outlet that is appropriate for delivery of the syringe contents through the delivery line when the delivery line is re-opened. In one or more embodiments in which, for example, the flow control device is in the form of a one-way check valve, the selected delivery force level may correspond to a pressure in the delivery line that is equal to or greater than the cracking (or opening) pressure of the one-way check valve.

The above actions may, of course be implemented using a syringe pump apparatus operated in the manner described above. With reference, for example, to the apparatus as depicted in FIG. 1, in one or more embodiments, the flow control device 14 in a syringe pump apparatus 10 may be configured to selectively prevent flow out of the syringe 20 (into, e.g., the delivery line 12). The control unit 40 may be configured to close the flow control device 14 to prevent flow out of the syringe 20. The control unit 40 may further be configured to move the plunger clip 30 toward the syringe retainer 16 using the drive system 32 while the flow control device 14 is closed. The control unit 40 may also be configured to measure the force exerted on the plunger clip 30 by the drive system 32 using the force sensor 34. Still further, the control unit 40 may be configured to make a determination that the syringe 20 is properly connected to, e.g., the delivery line 12 if the force measured by the force sensor while moving the plunger clip 30 towards the syringe retainer 16 reaches or exceeds a selected delivery force level. The control unit 40 may be configured to make a determination that the syringe 20 is not properly connected if the measured force does not reach or exceed the selected delivery force level after the plunger clip 30 has moved over a selected distance.

The addition of force sensors and/or displacement sensors on the plunger clips of the syringe pump apparatus described herein may, in one or more embodiments, also offer an opportunity to provide an automated movement feature without requiring the user to interface directly with the controls of the apparatus (e.g., a touchscreen, touchpad, switches, mouse, etc.). If a user wanted the plunger clip to move in the forward direction, the user could simply push the plunger clip in the forward direction. The control system could be configured to actuate the drive system to move the plunger clip in the forward direction as the plunger clip is moved in the forward direction because doing so would result in a force exerted on force sensor and/or displacement of the plunger clip that could be detected by the displacement sensor. Similar actions could happen if the user pushes the plunger clip in the reverse direction. In other words, the control system could be configured to actuate the drive system to move the plunger clip in the reverse direction as the plunger clip is moved in the reverse direction because doing so would result in a force exerted on force sensor and/or displacement of the plunger clip that could be detected by the displacement sensor.

The complete disclosure of the patents, patent documents, and publications identified herein are incorporated by reference in their entirety as if each were individually incorporated.

Illustrative embodiments of syringe pump apparatus configured to detect engagement between a drive system and a plunger of a syringe in the syringe pump apparatus and methods of using the same are discussed and reference has been made to possible variations. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A method of detecting engagement between a drive system and a plunger of a syringe in a syringe pump, the method comprising:
    moving a plunger clip away from a syringe retainer configured to retain a syringe in a fixed position;
    preventing flow into the syringe in the syringe retainer while moving the plunger clip away from the syringe retainer;
    measuring a force exerted on the plunger clip while preventing flow into the syringe; and
    determining that the plunger clip is properly engaged with the plunger of the syringe in the syringe retainer if the measured force reaches or exceeds a selected force level.

2. A method according to claim 1, wherein the method comprises determining that the plunger clip is not properly engaged with the plunger if the measured force has not reached the selected force level after moving the plunger clip a selected limit distance.

3. A method according to claim 1, wherein the selected force level is dependent on a distance over which the plunger clip moves, and wherein the selected force level increases as the distance increases.

4. A method according to claim 1, wherein the method comprises stopping movement of the plunger clip away from the syringe retainer when the selected force level is reached.

5. A method according to claim 1, wherein the method comprises measuring the force exerted on the plunger clip while moving the plunger clip.

6. A method according to claim 1, wherein preventing flow into the syringe comprises closing a flow control device.

7. A method according to claim 6, wherein the method comprises closing the flow control device before moving the plunger clip away from the syringe retainer.

8. A method according to claim 1, wherein the method comprises moving the plunger clip toward the syringe retainer to a selected position after determining that the plunger clip is properly engaged with the plunger of the syringe in the syringe retainer.

9. A method according to claim 8, wherein the selected position comprises a starting position of the plunger clip, wherein the starting position comprises a position of the plunger clip before moving the plunger clip away from the syringe retainer.

10. A method according to claim 1, wherein the method comprises:
moving the plunger clip toward the syringe retainer while preventing flow out of the syringe;
measuring the force exerted on the plunger clip by the drive system using the force sensor while moving the plunger clip toward the syringe retainer and preventing flow out of the syringe; and
determining that the syringe is properly connected to a delivery line if the force measured by the force sensor while moving the plunger clip towards the syringe retainer reaches or exceeds a selected delivery force level.

11. A method of detecting engagement between a drive system and a plunger of a syringe in a syringe pump, the method comprising:
moving a plunger clip away from a syringe retainer configured to retain a syringe in a fixed position;
preventing flow into the syringe in the syringe retainer while moving the plunger clip away from the syringe retainer, wherein preventing flow into the syringe comprises closing a flow control device;
measuring a force exerted on the plunger clip while preventing flow into the syringe; and
determining that the plunger clip is properly engaged with the plunger of the syringe in the syringe retainer if the measured force reaches or exceeds a selected force level;
determining that the plunger clip is not properly engaged with the plunger if the measured force has not reached the selected force level after moving the plunger clip a selected limit distance.

12. A method according to claim 11, wherein the selected force level is dependent on a distance over which the plunger clip moves, and wherein the selected force level increases as the distance increases.

13. A method according to claim 11, wherein the method comprises stopping movement of the plunger clip away from the syringe retainer when the selected force level is reached.

14. A method according to claim 11, wherein the method comprises measuring the force exerted on the plunger clip while moving the plunger clip.

15. A method according to claim 11, wherein the method comprises closing the flow control device before moving the plunger clip away from the syringe retainer.

16. A method according to claim 11, wherein the method comprises moving the plunger clip toward the syringe retainer to a selected position after determining that the plunger clip is properly engaged with the plunger of the syringe in the syringe retainer.

17. A method according to claim 16, wherein the selected position comprises a starting position of the plunger clip, wherein the starting position comprises a position of the plunger clip before moving the plunger clip away from the syringe retainer.

18. A method according to claim 11, wherein the method comprises:
moving the plunger clip toward the syringe retainer while preventing flow out of the syringe;
measuring the force exerted on the plunger clip by the drive system using the force sensor while moving the plunger clip toward the syringe retainer and preventing flow out of the syringe; and
determining that the syringe is properly connected to a delivery line if the force measured by the force sensor while moving the plunger clip towards the syringe retainer reaches or exceeds a selected delivery force level.

* * * * *